(12) United States Patent
Utsui et al.

(10) Patent No.: US 6,438,302 B1
(45) Date of Patent: Aug. 20, 2002

(54) ENDOSCOPE SYSTEM AND ILLUMINATING DEVICE FOR THE ENDOSCOPE

(75) Inventors: Tetsuya Utsui, Saitama-ken; Koichi Furusawa, Tokyo, both of (JP)

(73) Assignee: Asahi Kogaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/603,351

(22) Filed: Jun. 26, 2000

(30) Foreign Application Priority Data

Jun. 28, 1999 (JP) ............................................ 11-181296

(51) Int. Cl.[7] .............................. G02B 6/06; G02B 6/04; A61B 1/06
(52) U.S. Cl. ..................... 385/117; 385/116; 352/554; 600/182
(58) Field of Search ................................. 385/116, 117, 385/115, 120, 121; 600/178, 182; 362/554

(56) References Cited

U.S. PATENT DOCUMENTS

| 5,036,834 | A | | 8/1991 | Sugiyama et al. |
| 5,237,403 | A | | 8/1993 | Sugimoto et al. |
| 5,488,509 | A | | 1/1996 | Takahashi et al. |
| 5,746,494 | A | | 5/1998 | Koeda et al. |
| 6,112,004 | A | * | 8/2000 | Colvin ........................ 385/116 |
| 6,134,365 | A | * | 11/2000 | Colvin ........................ 385/116 |

FOREIGN PATENT DOCUMENTS

WO  99/37204  7/1999

* cited by examiner

Primary Examiner—Hemang Sanghavi
Assistant Examiner—Omar Rojas, Jr.
(74) Attorney, Agent, or Firm—Greenblum & Bernstein, P.L.C.

(57) ABSTRACT

An illuminating device for an endoscope system emits light toward a light receiving surface of an optical fiber bundle. Light incident on the light receiving surface of said optical fiber bundle is emitted from a light emitting surface of the optical fiber bundle for illuminating an object. The illuminating device is provided with a plurality of light emitting elements, each of which emits a directive monochromatic light beam. The light beams emitted by the plurality of light emitting elements are incident on the light receiving surface of the optical fiber bundle within an angular aperture of the light receiving surface thereof.

14 Claims, 4 Drawing Sheets

ENDOSCOPE SYSTEM AND ILLUMINATING DEVICE FOR THE ENDOSCOPE

BACKGROUND OF THE INVENTION

The present invention relates to an endoscope system, and an illuminating device to be employed in the endoscope system.

Figure 4:
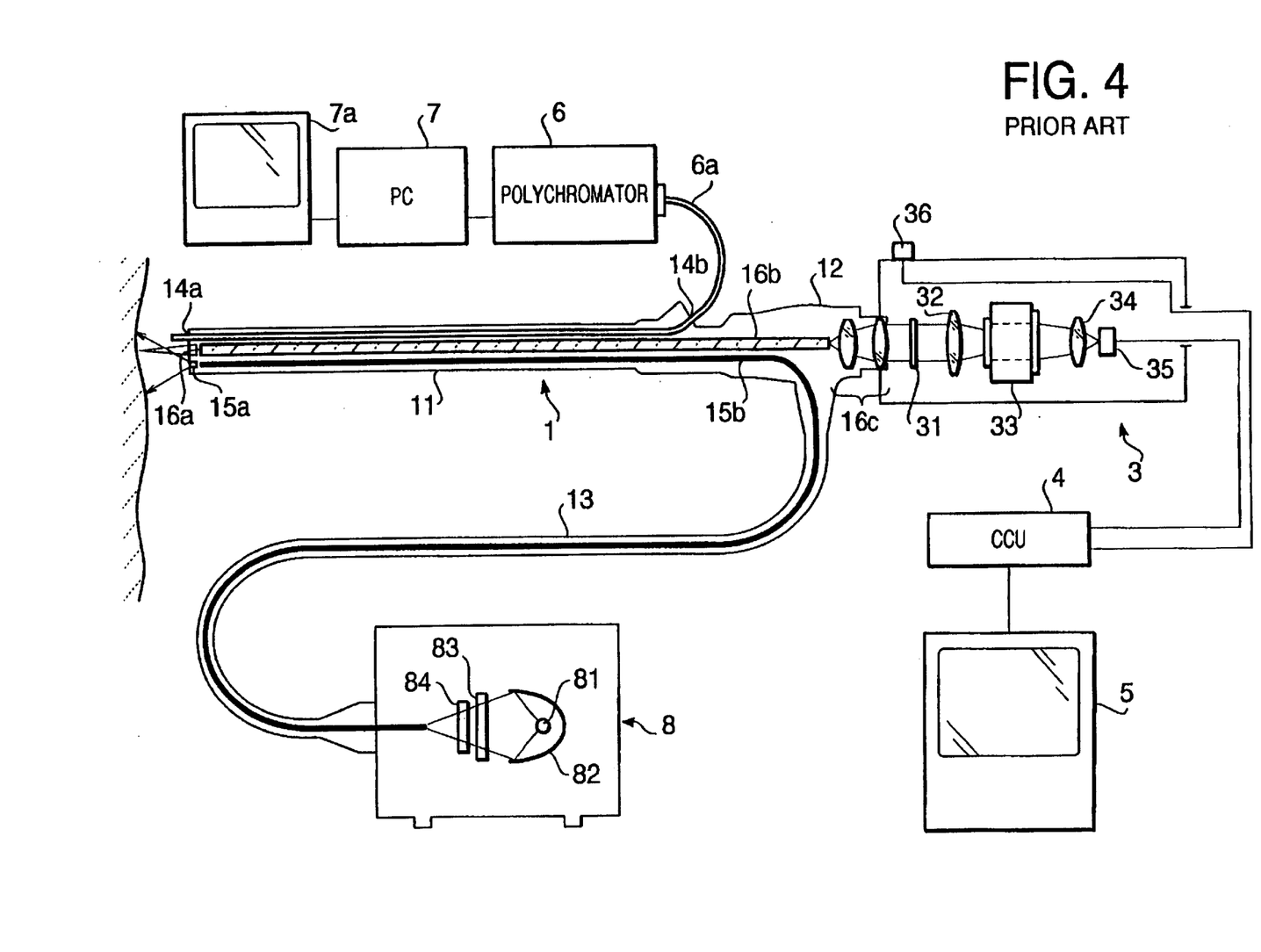
FIG. 4 shows a configuration of. a conventional fluorescent endoscope system.

It has been known that human tissues fluoresce when illuminated with excitation light. The wavelength range of the excitation light is a range of 380–480 nm, and the wavelength range of the fluorescent light emitted by the tissues is a range of 480–600 nm. The fluorescent light emitted by diseased tissues such as cancerous ones has less intensity than that emitted by normal tissues if they are illuminated with the predetermined excitation light. Therefore, conventionally, a fluorescent endoscope system utilizing-the above characteristics has been developed and used. Such an endoscope system has, as shown in FIG. 4, a fiber scope system 1, an illuminating device 8 connected to the fiber scope 1, and an image capturing device 3.

The fiber scope 1 includes an insertion portion 11 to be inserted in a human cavity, an operation unit 12 connected to the insertion portion 11. and a connecting tube 13 connected to the operation unit 12. At the distal end side surface of the insertion portion 11. three through openings are formed, one of which is used as a forceps outlet 14a, and an illumination lens 15a and an objective lens 16a are fitted in the other openings, respectively.

An end of the operation unit 12 is connected to the proximal end of the insertion portion 11. An eyepiece optical system 16c is accommodated in the operation unit 12. Inside the insertion portion 11 and the operation unit 12, an image guide fiber bundle 16b (hereinafter referred to as an image guide) is inserted. The image guide 16b is arranged such that the tip end surface thereof faces the objective lens 16a, and the proximal end surface faces the eyepiece optical system 16c.

An end of the connection tube 13 is connected to a side surface of the operation unit 12, and the other end of the connection tube 13 is connected to the illuminating device 8. Inside the insertion portion 11, the operation unit 12, and the connection tube 13, a light guide fiber bundle 15b (hereinafter referred to as a light guide) is inserted.

The Illuminating device 8 is provided with a xenon lamp 81, a reflector 82, an infrared cut off filter 83 and a light source side band pass filter 84. The xenon lamp 81 emits white light having a relatively large intensity. The reflector 82 is arranged such that the white light emitted by the xenon lamp 81 is reflected toward a light receiving surface of the light guide 15b as converging light. Between the xenon lamp 81 and the light receiving surface of the light guide 15b, the infrared cut out filter 83, which prevents radiation of heat by removing Infrared component within the white light, and the light source side band pass filter 84, which allows light having a predetermined wavelength range (e.g., 400 nm–450 nm) that corresponds to the wavelength range of an excitation light, are arranged.

Thus, the light emitted by the xenon lamp 81 and reflected by the reflector 82 enters the light guide 15b with the infrared components being removed by the infrared cut filter 83, and the components other than the excitation light being removed by the band pass filter 84.

The light conducted by the light guide 15b is emerged from a light emerging surface thereof. The light emerged form the light guide 15b is incident on the illumination lens 15a and emerged therefrom as a diverging excitation light. The excitation light Illuminates a wall of a human body cavity, thereby the illuminated portion of the body cavity fluoresces to emit fluorescent light. The fluorescent light emitted by the body cavity as well as the excitation light reflected by the body cavity is incident on the objective lens 16a. The objective lens 16a converges the incident light on the light receiving surface (i.e., the tip end surface) of the image guide 16b to form an image of the illuminated portion, which is transmitted to the eyepiece optical system through the image guide 16b.

In the image capturing device 3, an optical path along which the light emerged from the eyepiece optical system 16c is defined. The image capturing device 3 includes, along the optical path, a band pass filter 31, a condenser lens 32, an image intensifier 33, an imaging optical system 34 and a camera head 35.

The band pass filter 31 cuts off the reflected excitation light component so that only the fluorescent light component passes therethrough. The condenser lens 32 collects the light passed through the band pass filter 31 and converges the same to impinge on the image intensifier 33. The image intensifier 33 intensifies the incident light. The imaging optical system 34 converges the intensified light to form an image on an image receiving surface of the camera head 35. The camera head 35 converts the optical image formed on the image receiving surface into an electrical image (i.e., an electrical signal), and transmits the electrical signal to a camera control unit 4 (hereinafter referred to as CCU). The CCU 4 converts the electrical signal received from the camera head 35 into an image signal, and displays the image carried by the electrical signal on a monitor 5.

Further to the above, the conventional fluorescent endoscope system is provided with a polychromator 6, and a personal computer 7 connected to the polychromator 6. The polychromator 6 includes a light guide probe 6a. The polychromator 6 detects intensity of light incident on the tip end of the light guide probe 6a on wavelength basis.

The light guide probe 6a is inserted from a forceps inlet opened on the operation unit 12 and inserted through the fiber scope 1, the tip end of the light guide probe 6a being protruded out of the forceps outlet 14a of the insertion portion 11.

The polychromator 6 detects the intensity of the fluorescent light conducted by the light guide probe 6a on wavelength basis, converts the same into electrical signals, and outputs to the personal computer 7. The personal computer 7 displays a graph showing an intensity distribution of the fluorescent light on wavelength basis.

According to the conventional fluorescent endoscope system, the illuminating device 8 is constituted such that the white light is incident on the band pass filter 84 to obtain the excitation light. However, it is impossible to completely remove the components other than the excitation light component from the white light with the band pass filter 84. Therefore, in the conventional fluorescent endoscope system, the light components other than the excitation light component affect the image to be observed.

Alternative to the above-described illuminating device 8, an illuminating device employing a laser light source can be employed. Since the laser is superior in terms of monochromatism, the band pass filter 84 and the like are unnecessary. However, in order to obtain a sufficient intensity as the excitation light, the light source needs to be a large device such as a gas laser device. Further, such a laser device requires a relatively long idling period before it starts emitting light, the light source should be ready in advance, which is troublesome. Furthermore, when the gas laser device is used, an initial cost as well as a maintenance cost becomes relatively expensive.

SUMMARY OF THE INVENTION

It is therefore an object of the invention to provide an improved endoscope system employing an illuminating device which is superior in monochromatism, and can be used simply and quickly.

For the above object, according to the invention, there is provided an illuminating device for an endoscope system. The illuminating device emits light toward a light receiving surface of an optical fiber bundle. The light incident on the light receiving surface of the optical fiber bundle is emitted from a light emitting surface thereof for illuminating an object. The illuminating device is provided with a plurality of light emitting elements, each of which emits a directive monochromatic light beam. The light beams emitted by the plurality of light emitting elements are incident on the light receiving surface of the optical fiber bundle within an angular aperture thereof.

Since a plurality of light emitting elements which emit directive and monochromatic light beams, even if a light beam emitted by each light emitting element has relatively low intensity, the resultant light collected on the light receiving surface of the optical fiber bundle has sufficient intensity. Thus, monochromatic light beam having a sufficient intensity can be obtained with a relatively compact structure.

According to another aspect of the invention, there is provided an endoscope system, which is provided with an illuminating device, an endoscope, an optical fiber bundle having a light receiving surface and light emitting surface, the optical fiber bundle being inserted through the endoscope, and an illuminating optical system provided at a distal end portion of the endoscope. The light receiving surface of the optical fiber bundle faces the illuminating device, and the light emitting surface of the optical fiber bundle faces the illuminating optical system. The illuminating device is provided with a plurality of light emitting elements, each of which emits a directive monochromatic light beam. The light beams emitted by the plurality of light emitting elements are incident on the light receiving. surface of the optical fiber bundle within an angular aperture thereof. The light emitted from the light emitting surface of the optical fiber bundle is directed toward an object through the illuminating optical system.

Optionally, in either of the above illuminating device or the endoscope system, the plurality of light emitting elements may be arranged on a substantially spherical concave plane, whose center is located substantially on the central axis of the light receiving surface of the optical fiber bundle.

In this case, it is beneficial to provide a mount member on which the plurality of light emitting elements are fixed. The mount member may be provided with a surface formed to have the substantially spherical concave plane as defined above. The surface may face the light receiving surface of the optical fiber bundle, and the plurality of light emitting elements are mounted on the surface of the mount member.

With this structure, the optical path for each light emitting element can be adjusted easily.

In particular case, the plurality of light emitting elements are light emitting diodes. Alternatively, the plurality of light emitting elements are a plurality of laser diodes.

In particular, each of the plurality of light emitting elements emits a light beam whose wavelength is within a range of 380–480 nm, preferably, 400–450 nm. In this case, the emitted light is used as excitation light. The human tissues fluoresce upon incidence of the excitation light.

DESCRIPTION OF THE EMBODIMENT

Hereinafter, the invention will be described with reference to the accompanying drawings.

First Embodiment

Figure 1:
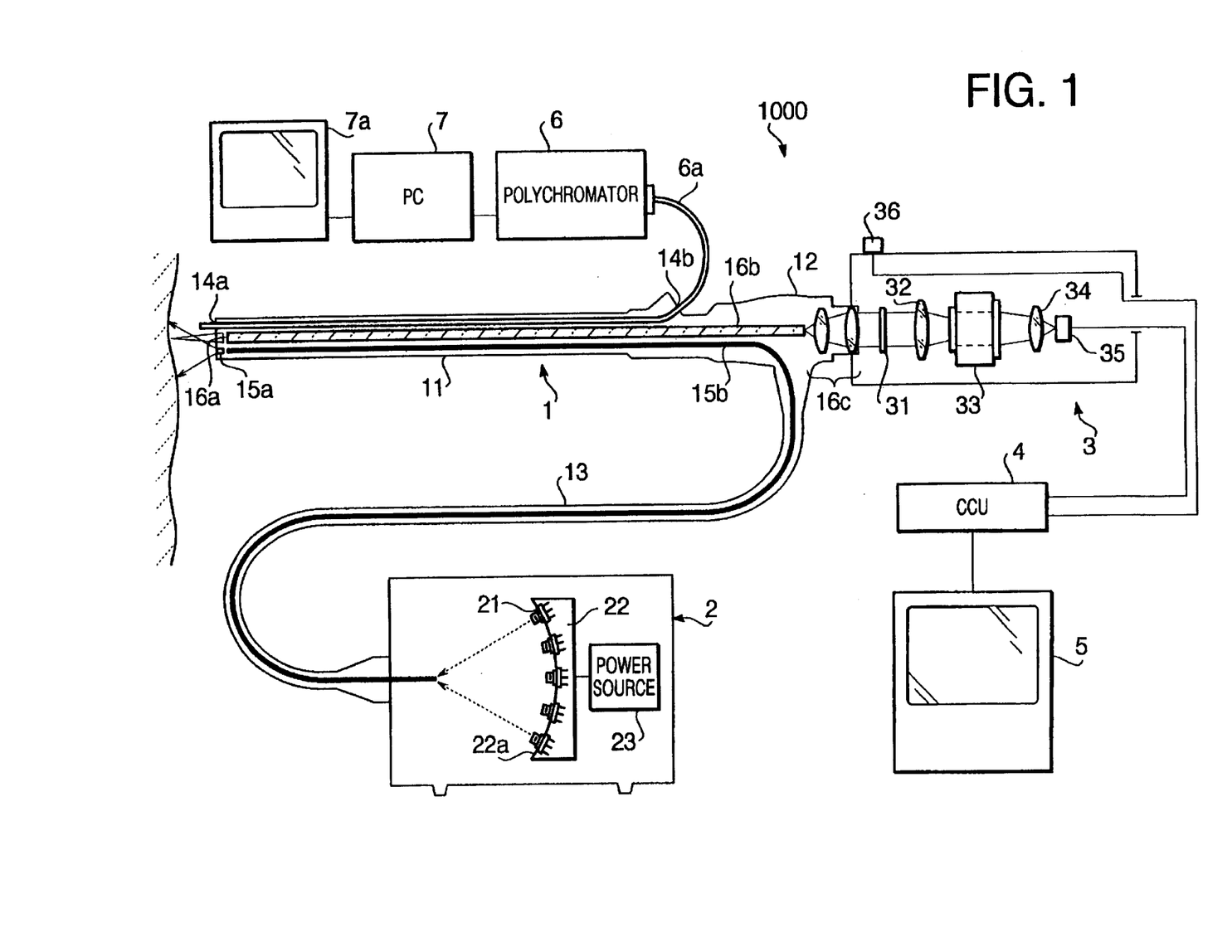
FIG. 1 schematically shows a configuration of a fluorescent endoscope system according to a first embodiment of the invention.

FIG. 1 shows a configuration of a fluorescent endoscope system 1000 according to a first embodiment of the invention.

The fluorescent endoscope system 1000 includes a fiber scope 1, an illuminating device 2 and an image capturing device 3, which are connected to the fiber scope 1.

The fiber scope 1 has an insertion portion 11 to be inserted in the human cavity. An operation unit 12 is connected to the insertion portion 11, and a connecting tube 13 is connected to the operation unit 12.

The insertion portion 11 is formed to be an elongated flexible tube, the distal end thereof being closed with a disk-like end surface. At least three openings are formed on the disk-like end surface of the insertion portion 11. One of the openings is used as a forceps outlet opening 14a. An illumination lens 15a and an objective lens 16a for observation are fitted in the other openings, respectively.

An end of the operation unit 12 is connected to the proximal end of the insertion portion 11, and a space communicating with the insertion portion 11 is formed inside the operation unit 12. An eyepiece optical system 16c is accommodated inside the operation unit 12, at the other end side. On the surface of the operation unit. various switches (not shown) for operations and settings of the endoscope system.

An image guide 16b is inserted through the insertion portion 11 and the operation unit 12. The image guide 16b is arranged such that the tip end surface thereof faces the objective lens 16a, and the other end surface (i.e., the proximal end surface) faces an eyepiece optical system 16c.

The objective lens 16a receives light from an objective portion, and converges the light on the tip end surface of the image guide 16b to form the image of the objective portion. The light converged on the tip end surface of the image guide 16b is directed inside the image guide 16, and emerged from the proximal end surface thereof toward the eyepiece optical system 16c. The eyepiece optical system 16c magnifies an image of an objective portion for observation.

On a side surface, at the distal end side, of the operation unit 12, a forceps inlet opening 14b is formed. The forceps inlet opening 14b and the forceps outlet opening 14a are connected with a not-shown tubular member which defines a forceps channel. With this structure, an instrument such as forceps, treatment accessories, probes and the like can be inserted through the forceps channel and protruded from the forceps outlet opening 14a.

The connecting tube 13 is a flexible tube, an end of which is connected to a side surface of the operation unit 12, and the other end of which is connected to the illuminating device 2. A light guide fiber bundle 15b (hereinafter referred to as light guide) is inserted through the insertion portion 11, the operation unit 12 and the connecting tube 13. The light guide 15b is composed of a plurality of densely bundled multi-mode optical fibers. The end surfaces, along its length, of the light guide 15b are formed as a light receiving surface and a light emitting surface. The light emitting surface of the light guide 15b faces an illumination lens 15a, and a light receiving surface side portion of the light guide 15b is inserted inside the illuminating device 2.

The illuminating device 2 emits excitation light having a predetermined wavelength within a range of 400–450 nm), which excites human tissues to fluoresce. The excitation light introduced by the light guide 15b is emitted from the light emitting surface thereof, passes through the illumination lens 15a, and is incident on a wall of a body cavity to be observed as a diverging light.

Next, the image capturing device 3 will be described. The image capturing device 3 is connected to the operation unit 12 such that the light passed through the eyepiece optical system 16c is introduced therein. The image capturing device 3 includes, along the optical path of the incident light, a band pass filter 31, a condenser lens 32, an image intensifier 33, an imaging optical system 34, and a camera head 35.

The band pass filter 31 only allows the fluorescent light emitted by the tissues, and prevent the reflected excitation light from passing therethrough. The condenser lens 32 collects light passed through the band pass filter 31, and directs the collected beam to the image intensifier 33. The image intensifier 33 amplifies the intensity of the incident beam, and emerges the light beam having the amplified intensity. The imaging optical system 34 converges the light beam emerged from the image intensifier 33 on an image receiving surface of the camera head 35 to form an image of an object thereon.

The camera head 35 of the image capturing device 3 is connected with a camera control unit 4 (hereinafeter referred to as a CCU). The CCU 4 is connected to a monitor device 5. The camera head 35 of the image capturing device 3 converts the received image into an electrical signal and transmits the signal to the CCU 4. The CCU 4 displays an image of the object in accordance with the electrical signal transmitted from the camera head 35.

The image capturing device 3 has a sensitivity control unit 36 provided on the outside surface of its casing. The sensitivity control unit 36 is connected to the CCU4 via a cable. An operator is capable of adjusting the brightness and/or contrast of the image displayed on the monitor device 5 by operating the sensitivity control unit 36 to control the CCU 4.

The fiber scope 1 enables an operator to observe an enlarged image of the object through the eyepiece optical system 16c when it is not connected to the image capturing device 3, and an object to be observed is illuminated with white light.

In the embodiment, however, the fiber scope 1 is connected to the image capturing device 3 such that the eyepiece optical system 16c faces the band pass filter 31 of the image capturing device 3. Thus, the eyepiece optical system 16c of the fiber scope 1. in association with the condenser lens 32 and the imaging optical system 34, relays the object image to the camera head 35.

Next, the Illuminating device 2 will be described.

The illuminating device 2 includes a plurality of light emitting elements 21, a mount 22 for mounting the light emitting elements 21, and a power source 23.

Figure 2:
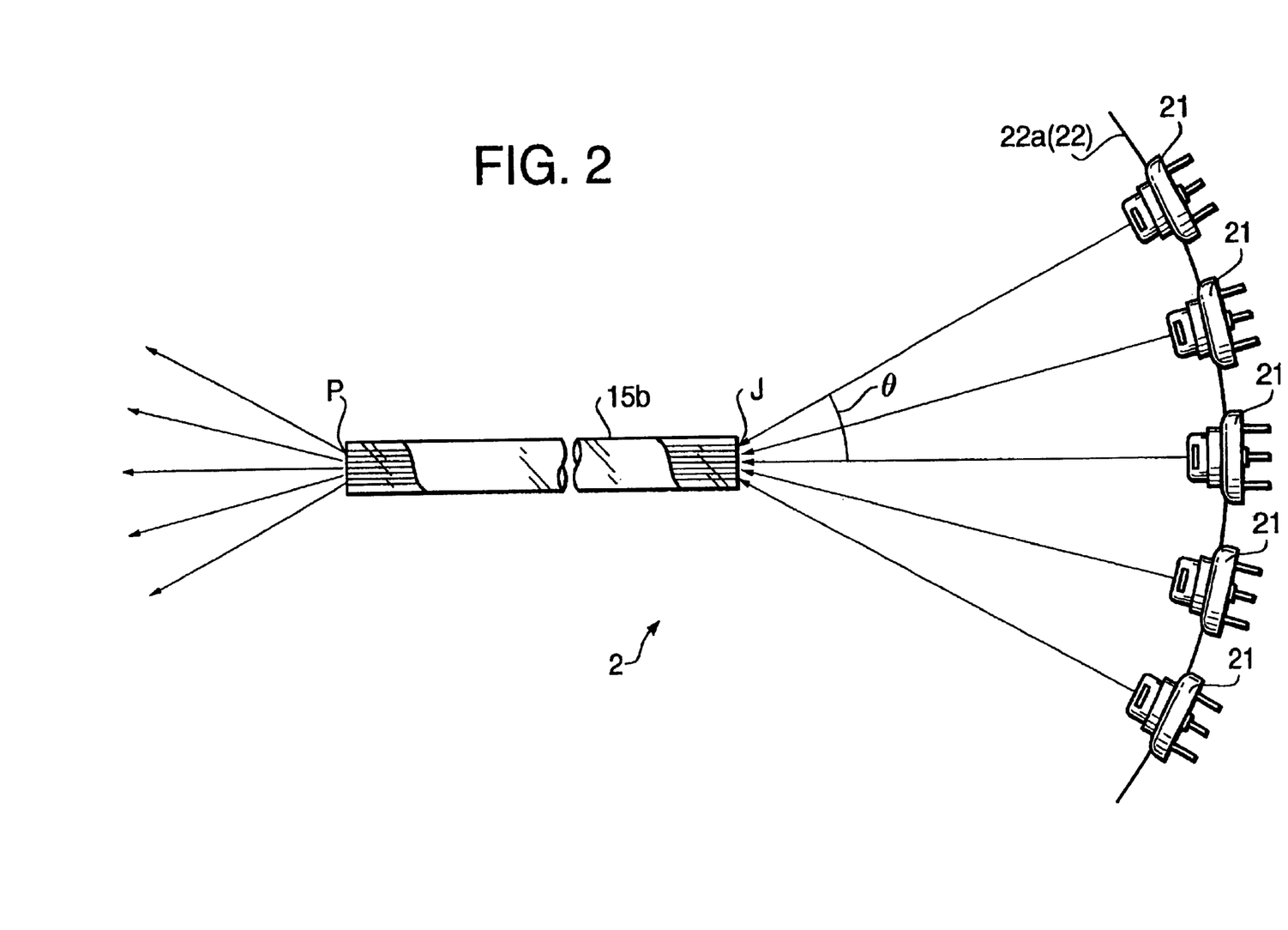
FIG. 2 schematically shows a illuminating device employed in the endoscope system according to the first embodiment of the invention.

FIG. 2 schematically shows a structure of the light emitting elements 21, the mount 22 and the light guide 15b. The light emitting elements 21 are LED's (light emitting diodes) for emitting blue light beams (monochromatic light) wavelength of which is 450 nm or less (approximately, within a range of 400–450 nm). Each light emitting element 21 has directivity so that the emitted beam proceeds directively in a predetermined direction. The beam emitted by each light emitting element 21 is utilized as the excitation light beam. It should be noted that the light emitting element 21 is not limited to ones emitting the blue light. Any light emitting elements will be used If the wavelength of the emitted light beam falls within a range of the excitation light which causes the human tissue to fluoresce (i.e., 400–450 nm).

The mount 22 has a substantially spherical concave surface 22a. The mount 22 is arranged such that the central axis of the concave surface 22a coincides with the central axis of the light guide 15b at the light receiving surface side, the concave surface 22a facing the light receiving surface J of the light guide 15b.

Imagine a cone whose apex is located at the center of the light receiving surface J of the light guide 15b, and flaring toward the concave surface 22a, the central axis of the cone coinciding with the central axis of the concave surface 22a, an angle $\theta$ formed between the central axis of the cone and a generatrix thereof being a half of an angular aperture of the light guide 15b (i.e., sin $\theta$ being equal to the numerical aperture NA of the light guide). The light emitting elements 21 are arranged on the concave surface 22a of the mount 22 such that a light beam emitted by each light emitting element 22 proceeds within the imaginary cone, and is incident on the light receiving surface J of the light guide 15b.

It should be noted that the concave surface 22a and the light emitting elements 21 are schematically shown in FIGS. 1 and 2. Actually, the light emitting elements 21 are distributed all over the concave surface 22a at predetermined interval.

Each light emitting element 21 is connected to the power source 23. The power source 23 supplies electrical current to the light emitting elements 21 individually to turn ON/OFF the light emitting elements 21. The excitation light beams emitted by the light emitting elements 21 impinge on the light receiving surface J of the light guide 15b within a range of the angular aperture of the light guide 15b as aforementioned.

With the above-described structure, a fluorescent light image of the object can be obtained. In the present embodiment, however, further to the above structure, a polychromator 6 is also employed. That is, the endoscope system 1000 further includes the polychromator 6 and a personal computer 7 connected to the polychromator 6. The polychromator 6 has a light guiding probe 6a, and detects the intensity of a light beam incident of the tip of the light guiding probe 6a.

The light guiding probe 6a is inserted from a forceps inlet 14b of the fiber scope 1. extending through the forceps channel inside the fiber scope 1. The tip end of the light guiding probe 6a is protruded from a forceps outlet 14a. The fluorescent light incident on the tip end portion of the light guiding probe 6a is introduced to the polychromator 6. The polychromator 6 detects the intensity of the fluorescent light incident on the tip of the light guiding probe 6a for each wavelength, converts the same into electrical signals, and transmits the electrical signals to the personal computer 7. The personal computer 7 processes the received signals, and displays a graph showing the wavelength-intensity distribution of the fluorescent light on a monitor 7a.

Hereinafter, an operation of the fluorescent endoscope system 1000 according the embodiment will be described.

When an operator turns ON a main power supply (not shown), the power source 23 of the illuminating device 2 supplies electrical currents to each light emitting element 21. Then the light emitting elements 21 starts emitting the excitation light beams. The excitation light beams are incident on the light receiving surface J within the angular aperture of the light guide 15b, guided therein, and emerged from the light emitting surface P. The light beams emitted from the light emitting surface P are incident on the illumination lens 15a.

At this stage, the operator may insert the insertion section 11 of the fiber scope 1 in a human cavity. Then, the operator may adjust the insertion section 11 such that the tip end surface of the insertion section 11 faces the object, or a portion of the cavity wall to be observed. At this stage, the excitation light beams emerged from the illumination lens 15a illuminate the object. Then, the tissues of the object fluoresce. The fluorescent light and the reflected excitation light beams are incident on the objective lens 16a. The objective lens 16a converges the incident light beams to form an image of the object on the tip end surface of the image guide 16b. The image guide 16b guides the optical image, i.e., the incident fluorescent light and the reflected excitation light, which are then emerged from a proximal end surface of the image guide 16b. The eyepiece optical system 16c receives the light emerged from the image guide 16b, and makes the received light impinge on the band pass filter 31 of the image capturing device 3.

The band pass filter 31 does not allow the excitation light to pass through. and allows only the fluorescent light to pass therethrough. Therefore, only the fluorescent light is incident on the image intensifier 33. The image intensifier 33 amplifies the intensity of the incident florescent light and emerges the same. The imaging optical system 34 converges the intensified light on the image receiving surface of the camera head 35 to form the fluorescent object image thereon. The camera head 35 converts the received optical image into an electrical signal, and transmits the same to the CCU 4. The CCU 4 generates a video signal based on the received signal, and transmits the video signal to the monitor 5. Thus, the fluorescent object image is displayed on the monitor 5.

The operator can recognize a condition of the objective wall of the cavity by observing the fluorescent image displayed on the monitor 5. That is, the operator may determine that the portion of the fluorescent image, which is darker than the other portion, may be diseased. The operator can utilize the spectral intensity distribution of the fluorescent light obtained by the polychromator 6 and displayed on the monitor 7a.

As described above, according to the illuminating device 2 of the fluorescent endoscope system 1000, a filter for shielding the light other than the excitation light is not necessary, since the light emitting elements 21 emit a monochromatic light having the wavelength of the excitation light. Further, since the excitation light is monochromatically superior, light having a certain wavelength which obstacles the observation of the object will not emerged from the illumination lens 15a. Therefore, the operator can always observe the fluorescent object image in condition, which improves the accuracy of the diagnosis. Further, since the light emitting elements 21 are relatively small, the illuminating device 2 can be made compact.

Although the quantity of light emitted by a single light emitting element 21 is relatively small, since a plurality of light emitting element 21 are driven to emit light beams simultaneously. sufficient light amount is achieved. Further, all the excitation light beams are incident on the light guide 15b within the angular aperture of the light guide 15b, the sufficient amount of light can be obtained efficiently.

Further, the light emitting elements 21 stablly emit the light beams as soon as they are turned ON. Therefore, no idling time is required for operation, and preparation and maintenance procedures can be shortened significantly.

Second Embodiment

Figure 3:
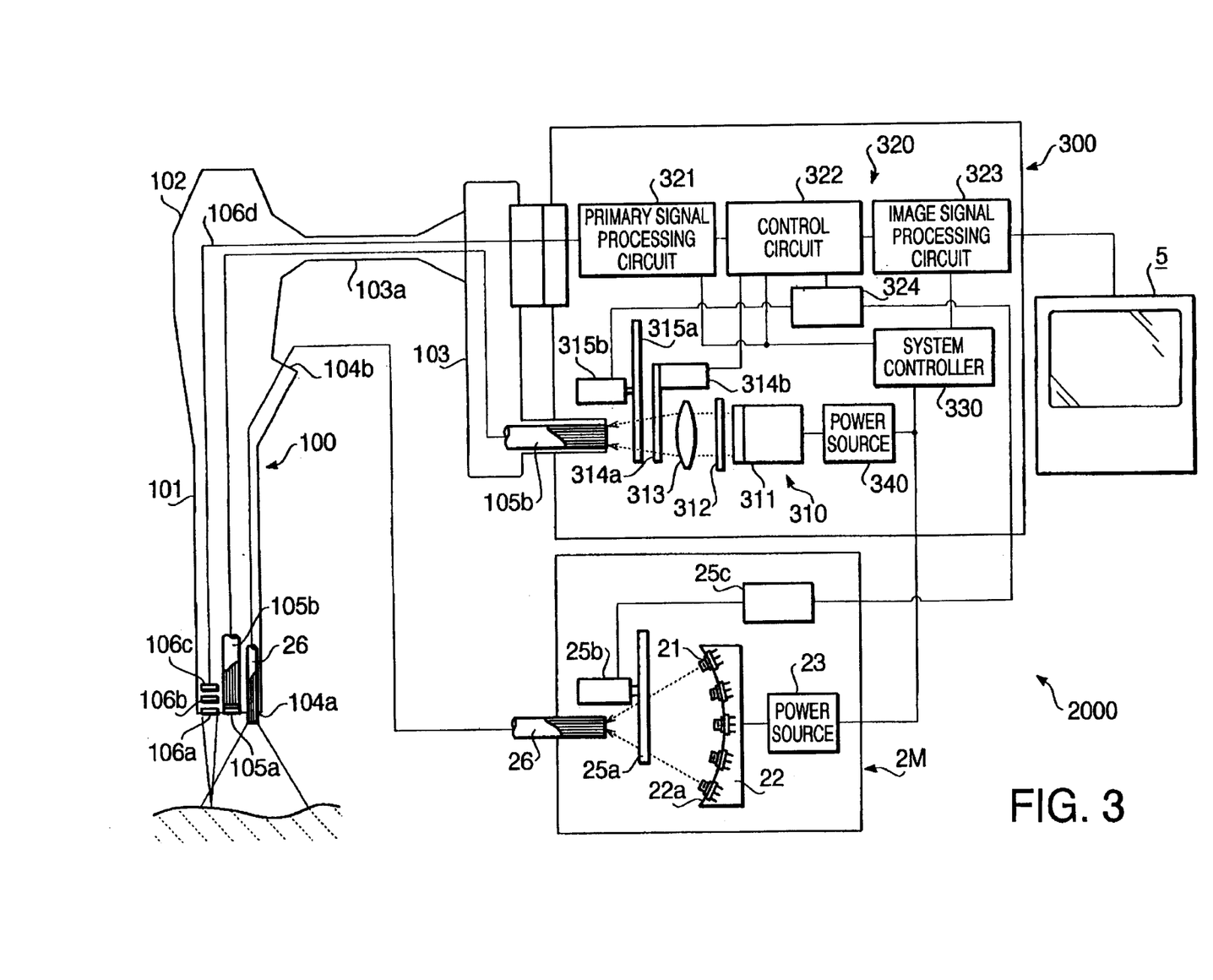
FIG. 3 shows a configuration of a fluorescent endoscope system according to a second embodiment of the invention.

The fluorescent endoscope system according to the second embodiment will be described. FIG. 3 shows the florescent endoscope system 2000, which includes an electronic endoscope 100, an external device 300 connected to the endoscope 100, an illuminating device 2M for emitting the excitation light, and a monitor 5.

The electronic endoscope 100 has an insertion portion 101, an operation unit 102 connected to the insertion portion 101, and a connecting unit 103 connected to the operation unit 102. The insertion portion 101 is formed to be an elongated flexible tube, the distal end thereof being closed with a disk-like end surface. At least three openings are formed on the disk-like end surface of the insertion portion 101. One of the openings is used as a forceps outlet opening 104a. A light illumination lens 105a and an objective lens 106a for observation are fitted in the other openings, respectively.

One end of the operation unit 102 is connected to the proximal end of the insertion portion 101. On the outer surface of the operation unit 102, a plurality of switches for operating and setting the endoscope system 2000 are provided. On the side surface of the operation unit 102, at the tip end side portion thereof, a forceps inlet 104b is opened. The forceps inlet 104b and the forceps outlet 104a are connected with a forceps channel. A treatment accessories inserted from the forceps inlet 104b is protruded from the forceps outlet 104a, via the forceps channel.

The connecting unit 103 is connected to the external device 300, and is connected to the operation unit 102 through a flexible connecting tube 103a. A light guide fiber bundle 105b (hereinafter referred to as light guide) is inserted through the insertion portion 101, the operation unit 102 and the connecting unit 103. The light guide 105b is composed of a plurality of multi-mode optical fibers densely bundled. The tip end surfaces of the light guide 105b are formed as a light receiving surface and a light emitting surface. The light emitting surface of the light guide 105b faces the illumination lens 105a, and a light receiving surface side portion of the light guide 105b is inserted inside the external device 300. In FIG. 3, the light guide 105b is schematically shown. That is, although the light guide 105b is represented by a single line in FIG. 3, the light guide 105b is actually a bundle of optical fibers and having a certain diameter over its length.

Inside a portion adjacent to the tip end of the insertion portion 101, a band pas filter 106b and an image capturing element 106c are provided to face the objective lens 106a. Inside the insertion portion 101, the operation unit 102, and the connecting unit 103, a signal line 106d is inserted. An end of the signal line 106d is connected to the image capturing element 106c and the other end thereof is inserted into the external device 300.

The band pass filter 106b is formed such that it allows the fluorescent light of the human tissues to pass therethrough, and prevents the excitation light from passing through. The image capturing element 106c is composed of a CCD (Charge Coupled Device), which converts the optical image formed thereon into an image signal. The image capturing element 106c is arranged such that the image receiving surface thereof is substantially coincident with the image plane of the objective lens 106a. The image capturing element 106c performs photoelectric conversion within a predetermined imaging period, and outputs the converted electrical signal (image signal) to the signal line 106d within a subsequent transferring period. The imaging period and the transferring period are repeated. and thus, image capturing and signal transferring are repeated.

Next, the external device 300 will be described.

The external device 300 includes a normal light source unit 310, a processor unit 320, a system control unit 330, and a power source 340. The power source 340 is connected to the normal light source unit 310, the processor unit 320 and the system control unit 330, to supply electricity thereto.

The normal light source unit 310 has a white light source 311 for emitting the white light. The normal light source unit 310 further includes, on the optical path of the light emitted by the light source 311, an infrared cut-off filter 312 a light collecting lens 313, an aperture 314a and a rotatable filter 315a.

The infrared cut-off filter 312 removes the infrared component from the light so as to prevent the radiation of heat from the normal light source unit 310.

The light collecting lens 313 converges the light emerged from the infrared cut-off filter 312 on the light receiving surface of the light guide 105b.

The aperture 314a and the roatatable filter 315a are arranged within a optical path between the light collecting lens 313 and the light receiving surface of the light guide 105b. The aperture 314a is connected with an aperture control mechanism 314b, which drives the aperture 314a to change the aperture size to control the amount of light.

The rotatable filter 315a is a disk-like rotatable member formed with a fan-shaped RGB (Red, Green and Blue) filters, which are arranged at the same angular interval. Portions of the disk-like rotatable member other than the color filters are formed to be opaque portions that shield the light. The rotatable filter 315a is coupled to a filter driving motor 315b. By driving the filter driving motor 315b, the Red, Green and Blue filters can be inserted in the optical path in this order. The filter driving motor 315b can also locate the opaque portion of the rotatable filter 315a at the optical path.

The processing unit 320 includes a primary signal processing circuit 321, a control circuit 322, and an image signal processing circuit. The primary signal processing circuit 321 is connected to the image capturing element 106c via the signal line 106d, and capable of holding the signal at a predetermined timing. Further, the primary signal processing circuit 321 applies various signal processing operations such as amplification, adjustment of a white balance, gamma correction, A/D conversion and the like, and then transmits the processed signal to the control circuit 322.

The control circuit 322 includes an RGB memory (not shown) and a timing controller. The RGB memory of the control circuit 322 has a B area, G area and R area. The RGB memory is capable of storing data corresponding to one screen image of the monitor 5. the RGB areas storing RGB components, respectively. The timing controller of the control circuit 322 generates various reference signals. The signal processing operations performed by the signal processing unit 320 is controlled in accordance with the reference signals generated by the timing controller.

It should be noted that the control circuit 322 writes the signal output by the primary signal processing circuit 321 in the RGB memory in accordance with a reference signal output by the timing controller.

The image signal processing circuit 323 is connected to the monitor 5, and obtains the data stored in the RGB memory of the control circuit 322 at a predetermined timing. Then, the image signal processing circuit 323 applies a various processing operations such as D/A conversion and an encoding for a predetermined TV format. The monitor 5 receives the processed video signal and display the image carried thereby.

The processing unit 320 further includes a first driver circuit 324 connected to the control circuit 322. The first driver circuit 324 is connected to the filter drive motor 315b of the normal light source unit 310. The control circuit 322 controls the filter drive motor 315b through the driver circuit 324 so that the rotatable filter 315a rotates at a predetermined speed. The control circuit 322 is also connected to the aperture control mechanism 314b of the normal light source unit 310. The control circuit 322 controls the aperture 314a through the aperture control mechanism 314b to control the light amount.

The system control unit 330 is connected the primary signal processing circuit 321, the control circuit 322 and the image signal processing circuit 323 via the signal transmission line. Further, the system control unit 330 is connected to the operation unit 102 of the electronic endoscope 100, and the illuminating device 2M via the signal line (not shown), and controls the entire system.

Next, the illuminating device 2M for emitting the excitation light will be described.

The illuminating device 2M includes the light emitting elements 21, the mount 22 and the power source 23 which are similar to those employed in the first embodiment. Further, the illuminating device 2M has a rotary shutter 25a, a shutter drive motor 25b, a second driver circuit 25c and a light guide probe 26.

The light guide probe 26 includes an elongated flexible thin tube, and a fiber bundle arranged inside the thin tube. Specifically, the fiber bundle is composed of a plurality of multi-mode optical fiber densely bundled. An end of the light guide probe 26 is formed as a light receiving surface and the other end surface is formed as a light emitting surface. In FIG. 3, the light guide probe 26 is schematically shown and represented by a single line. However, the light guide probe 26 actually has a certain diameter over its entire length.

The light receiving surface side portion of the light guide probe 26 is inserted in the illuminating device 2M. The light receiving surface of the light guide probe 26 arranged at a position corresponding to the light receiving surface of the light guide 15b of the first embodiment. The light emitting surface side portion of the light guide probe 26 is inserted through the forceps inlet 104b and protruded from the forceps outlet 104a.

The rotary shutter 25a has a disk-like rotatable member formed with an opening (not shown). The rotary shutter 25a is inserted in the optical path between the light emitting elements 21 and the light receiving surface of the light guide probe 26. When the opening is located at the optical path, the excitation light beams emitted by the light emitting elements 21 pass through the opening and impinge on the light receiving surface of the light guide probe 26. When the opaque portion (i.e., the portion of the rotary shutter 25a other than the opening) is inserted in the optical path, the excitation light beams are shielded by the rotary shutter 25a.

The rotary shutter 25a is coupled to the shutter drive motor 25b, which is connected to the second driver circuit 25c via the signal line. The second driver circuit 25c controls the shutter drive motor 25b to rotate the rotary shutter 25a at a predetermined speed. The rotary shutter 25a, as being rotated at the predetermined speed, intermittently allows the excitation light beams to pass through the opening and impinge on the light incident surface of the light guide probe 26. Alternative to the above structure, it is possible to directly drive the light emitting elements 21 to be turned on intermittently with the power source 23.

The second driver circuit 25c is connected to the first driver circuit 324 of the processing unit 320. Therefore, the control circuit 322 of the processing unit 320 is capable of controls the second driver circuit 25c of the illuminating device 2M via the first driver circuit 324.

Operation of the above-constructed endoscope system will be described.

When an operator turns ON the main power source (not shown) of the endoscope system 2000, the power source 340 of the normal light source unit 310 of the external device 300 supplies electrical current to the white light source 311. The first driver circuit 324 controls the filter drive motor 315b to rotate the rotatable filter 315a at a constant speed. At an initial stage, the light emitting elements 21 of the illuminating device 12M are turned OFF, and the rotary shutter 25a is not rotated.

The white light emitted by the white light source 311 passes through the infrared filter 312, which eliminates the infrared component, the aperture 314a which adjust the light amount, and is directed to the rotatable filter 315a. The rotatable filter 315a is rotated and the color filters are inserted in the optical path sequentially so that the Blue, Green and Red light is emitted therefore, sequentially. The Blue, Green and Red light is sequentially converged on the light receiving surface of the light guide 105b. The light guided inside the light guide 105b is emerged from the light emitting surface of the light guide 105b, and then diverged by the illumination lens 105a.

It should be noted that the control circuit 322 of the processing unit 320 controls the first driver circuit 324 to operate synchronously with the imaging and transferring periods of the image capturing element 106c of the electronic endoscope 100. That is, the first driver circuit 324 controls the rotation speed of the rotatable filter 315a via the filter drive motor 315b such that: a predetermined portion of a period during which the Blue light is emitted from the illumination lens 105a corresponds to the imaging period of the image capturing element 106c, and the transferring is finished before the Green light is emitted; when the Green light is emitted, the imaging and transferring for the green image are completed; and when the Red light is emitted, the imaging and transferring for the red image are completed.

At this stage, the operator may insert the insertion portion 101 of the electronic endoscope 100 in the human cavity, and faces the tip end surface of the insertion portion 101 to the object, or a portion of the cavity wall to be observed. The Blue, Green and Red light are sequentially emerged from the illumination lens 105a and illuminate the cavity wall. The light reflected by the cavity wall enters the objective lens 106a, passes through the band pass filter 106b, and is converged on the image receiving surface of the image capturing element 106c. Accordingly, on the image receiving surface of the image capturing element 106c, the blue component, green component and red component of the object image are sequentially formed. The image capturing element 106c performs photo-electric conversion within the imaging period and transfers the converted signal within the transferring period to the signal line 106d.

The primary signal processing circuit 321 of the processing unit 320 of the external device 300 receives the signal from the imaging element 106c through the signal line 106c. Then, the primary signal processing circuit 321 amplifies the received signal, applies various signal processing operations, performs A/D conversion, and then stored the same in the RGB memory of the control circuit 322 as image data. That is, the signal obtained when the blue light is emitted is stored in the B area, the signal obtained when the green light is emitted is stored in the G area, and the signal obtained when the red light is emitted is stored in the R area of the RGB memory.

The image signal processing circuit 323 obtains the data stored in the RGB memory of the control circuit 322 at a predetermined timing, performs D/A conversion, encodes in accordance with the TV system, and displays the object image on the monitor 5. The operator can perform the normal observation of the object by viewing the image displayed on the monitor 5.

Further, the operator can observe the fluorescent image of the object. The fluorescent image can be displayed by operating a predetermined switch (not shown) provided on the operation unit 102.

Upon operation of the switch of the operation unit 102, the system control unit 330 detects that the operator indicated the fluorescent image observation. The system control unit 330 controls, via the first driver circuit 324 and the filter drive motor 315b, the rotatable filter 315a such that the opaque portion thereof is inserted in the optical path. With this control, the white light emitted by the white light source 311 is shielded by the opaque portion of the rotatable filter 315a, and is not incident on the light guide 105b.

At the same time, the system control unit 330 controls the power source 23 of the illuminating device 2M to light the light emitting elements 21, and rotates the rotary shutter 25a via the second driver circuit 25c and the shutter drive motor 25b.

It should be noted that the control circuit 322 of the processing unit 320 controls the second driver circuit 25c of the illuminating device 2M to operate synchronously with the imaging and transferring periods of the image capturing element 106c. That is, the second driver circuit 25c controls the rotating speed of the rotary shutter 25a, via the shutter driving motor 25b, such that a period, during which the opening of the rotary shutter 25a is located within the optical path, corresponds to the imaging period of the image capturing element 106c, and a period, during which the opening of the rotary shutter 25a is out of the optical path, corresponds to the transferring period of the image capturing element 106c.

Thus, the excitation light emitted by the light emitting elements 21 intermittently incident on the light receiving surface of the light guide probe 26. The excitation light guided by the light guide probe 26 is emerged to the cavity wall. Thus, the cavity wall is illuminated by the excitation light intermittently.

The cavity wall fluoresces when illuminated with the excitation light. The objective lens 106a collects the fluorescent light as well as the reflected excitation light. The band pass filter 106b prevents the reflected excitation light from passing therethrough, and allows the fluorescent light to pass through. The fluorescent light passed through the band pass filter 106b is converged on the image receiving surface of the image capturing element 106c, and forms the fluorescent object image.

When the fluorescent object image is formed on the image capturing element 106c, it operates in the imaging period, and thus, the optical image is converted in the electrical image signal. When the imaging period is finished and the transferring period starts, the rotary shutter 25a shields the excitation light. Accordingly, during the transferring period of the image capturing element 106c, the excitation light is not emerged from the illumination lens 105a. During the transferring period, the image capturing element 106c outputs the image signal corresponding to the fluorescent light image to the signal line 106d.

The primary signal processing circuit 321 receives the signal transmitted from the image capturing element 106c via the signal line 106d. Then, the primary signal processing circuit 321 amplifies the signal, performs various signal processing operations and A/D conversion. The primary signal processing circuit 321 stores thus obtained data in the RGB memory of the control unit 322.

The image signal processing circuit 323 obtains the data stored in the RGB memory of the control circuit 322 at a predetermined timing, performs D/A conversion and encoding in accordance with the TV system. and displays the fluorescent object image on the monitor 5. It should be. noted that the fluorescent image may be modified to an image colored in accordance with the intensity of fluorescent light.

By observing the image displayed on the monitor 5, the operator may recognize the condition of the object. For example, if there is a portion having lower brightness than the other portion, it may be determined to be a diseased portion.

By operating a switch on the operation unit 102, the endoscope system 2000 may be set to the-initial condition so that the normal observation is performed. That is, the system control unit 330 rotates the rotatable filter 315a at a constant speed via the first driver circuit 324 and the filter drive motor 315b upon detecting the operation of the switch. At the same time, the system control unit 330 controls the power source 23 of the illuminating device 2M to turn OFF the light emitting elements 21. As described above, the operator can switch the normal image observation mode and the fluorescent image observation mode arbitrarily.

It should be noted that the wavelength range of the excitation light can be a range of 380–480 nm, and preferably, 400–450 nm.

The present disclosure relates to the subject matter contained in Japanese Patent Application No. HEI 11-181296, filed on Jun. 28, 1999, which is expressly incorporated herein by reference in its entirety.

What is claimed is:

1. An illuminating device for an endoscope system, said illuminating device emitting light toward a light receiving surface of an optical fiber bundle, light incident on the light receiving surface of said optical fiber bundle being emitted from a light emitting surface of said optical fiber bundle for illuminating an object, said illuminating device comprising:
   a plurality of light emitting elements, arranged in a substantially spherical concave configuration, a center of said spherical concave configuration being substantially on a central axis of the light receiving surface of said optical fiber bundle, each of said plurality of light emitting elements emitting a directive monochromatic light beam, the light beams emitted by said plurality of light emitting elements being incident on the light receiving surface of said optical fiber bundle within an angular aperture of the light receiving surface of said optical fiber bundle.

2. The illuminating device according to claim 1, further comprising a mount member on which said plurality of light emitting elements are fixed, said mount member comprising a surface correlating to said substantially spherical concave configuration, said surface facing the light receiving surface of said optical fiber bundle, said plurality of light emitting elements being mounted on said surface of said mount member.

3. The illuminating device according to claim 1, wherein said plurality of light emitting elements are light emitting diodes.

4. The illuminating device according to claim 1, wherein said plurality of light emitting elements are a plurality of laser diodes.

5. The illuminating device according to claim 1, wherein each of said plurality of light emitting elements emits a light beam whose wavelength is within a range of 380–480 nm.

6. The illuminating device according to claim 5, wherein each of said plurality of light emitting elements emits a light beam whose wavelength is within a range of 400–450 nm.

7. An endoscope system, comprising:
   an illuminating device;
   an endoscope;
   an optical fiber bundle comprising a light receiving surface and light emitting surface, the optical fiber bundle being insertable through said endoscope; and
   an illuminating optical system provided at a distal end portion of said endoscope;
   wherein the light receiving surface of said optical fiber bundle faces said illuminating device and the light emitting surface of said optical fiber bundle faces said illuminating optical system; and
   wherein said illuminating device comprises a plurality of light emitting elements, arranged in a substantially spherical concave configuration, a center of said spherical concave configuration being substantially on a central axis of the light receiving surface of said optical fiber bundle, each of said plurality of light emitting elements emitting a directive monochromatic light beam, the light beams emitted by said plurality of light emitting elements being incident on the light receiving surface of said optical fiber bundle within an angular aperture of the light receiving surface of said optical fiber bundle, and light emitted from the light emitting surface of said optical fiber bundle being directed toward an object through said illuminating optical system.

8. The illuminating device according to claim 7, further comprising a mount member on which said plurality of light emitting elements are fixed, said mount member comprising a surface correlating to said substantially spherical concave configuration, said surface facing the light receiving surface of said optical fiber bundle, said plurality of light emitting elements being mounted on said surface of said mount member.

9. The illuminating device according to claim 7, wherein said plurality of light emitting elements are light emitting diodes.

10. The illuminating device according to claim 7, wherein said plurality of light emitting elements are a plurality of laser diodes.

11. The illuminating device according to claim 7, wherein each of said plurality of light emitting elements emits a light beam whose wavelength is within a range of 380–480 nm.

12. The illuminating device according to claim 11, wherein each of said plurality of light emitting elements emits a light beam whose wavelength is within a range of 400–450 nm.

13. An illuminating device for an endoscope system, said illuminating device emitting light toward a light receiving surface of an optical fiber bundle, light incident on the light receiving surface of said optical fiber bundle being emitted from a light emitting surface of said optical fiber bundle for illuminating an object, said illuminating device comprising:

a plurality of light emitting elements, each of said plurality of light emitting elements emitting a directive monochromatic light beam that is incident on the light receiving surface of said optical fiber bundle at a corresponding angle of incidence with respect to a central axis of the light receiving surface of said optical fiber bundle, a largest angle of the angles of incidence, corresponding to the light beams emitted by the plurality of light emitting elements, including a sine equal to a numerical aperture of said optical fiber bundle.

14. An endoscope system, comprising:

an endoscope;

an illuminating device, comprising a plurality of light emitting elements that emit a corresponding plurality of directive monochromatic light beams;

an illuminating optical system provided at a distal end portion of said endoscope; and an optical fiber bundle extending through said endoscope, the optical fiber bundle comprising a light receiving surface and light emitting surface, the light receiving surface facing said illuminating device and the light emitting surface facing said illuminating optical system;

the plurality of light beams of said plurality of light emitting elements being incident on the light receiving surface of said optical fiber bundle at a corresponding plurality of angles of incidence with respect to a central axis of the light receiving surface of said optical fiber bundle, a largest angle of incidence of the plurality of angles of incidence having a sine equal to a numerical aperture of said optical fiber bundle.

* * * * *